United States Patent [19]

Sawaki et al.

[11] 3,989,737

[45] Nov. 2, 1976

[54] 2-CYCLOHEXENE-1-ONE DERIVATIVES

[75] Inventors: Mikio Sawaki, Takaoka; Isao Iwataki, Odawara; Yoshihiko Hirono, Hiratsuka; Hisao Ishikawa, Odawara, all of Japan

[73] Assignee: Nippon Soda Company Limited, Tokyo, Japan

[22] Filed: Dec. 11, 1974

[21] Appl. No.: 531,810

[30] Foreign Application Priority Data

Dec. 24, 1973 Japan............................. 48-143556

[52] U.S. Cl. .................................. 260/472; 71/88;
71/90; 71/98; 71/103; 71/106; 71/107;
71/108; 71/111; 71/121; 260/332.2 R;
260/332.3 R; 260/347.2; 260/347.4; 260/456
R; 260/456 P; 260/468 J; 260/473 R;
260/477; 260/490; 260/566 AE
[51] Int. Cl.² .................................. C07C 131/08
[58] Field of Search ............... 260/477, 473 R, 472;
71/108, 111, 107, 98

[56] References Cited
UNITED STATES PATENTS 3,927,034   12/1975   Sawaki et al..................... 260/343.5

*Primary Examiner*—Jane S. Myers
*Attorney, Agent, or Firm*—George B. Oujevolk

[57] ABSTRACT
A compound of the formula

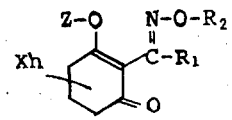

wherein
$R_1$ is selected from the group consisting of phenyl and straight or branched chain alkyl;
$R_2$ is selected from the group consisting of straight or branched chain lower alkyl, straight or branched chain lower alkenyl, lower alkynyl, lower alkoxymethyl, lower alkylthiomethyl and benzyl;
X is a same or different substituent which is selected from the group consisting of straight or branched chain alkyl, lower alkoxycarbonyl, phenyl, substituted phenyl having at least one substituent selected from the group consisting of halogen, methyl and methoxy, styryl, furyl, thienyl and —$(CH_2)_m$— in which $m$ is an integer from 1 to 6;
$n$ is 0 or an integer from 1 to 6;
Z is a substituent selected from the group consisting of R-A- and T in which R is selected from the group consisting of lower alkyl, phenyl, substituted phenyl having at least one substituent selected from the group consisting of halogen, methyl, methoxy and nitro, benzyl, phenoxymethyl and phenoxymethyl substituted with at least one halogen;
A is selected from the group consisting of carbonyl and sulfonyl;
T is selected from the group consisting of lower alkyl and benzyl;

is useful as herbicide.

20 Claims, 7 Drawing Figures

2-CYCLOHEXENE-1-ONE DERIVATIVES

DETAILED DESCRIPTION OF THE INVENTION

Figure 1:
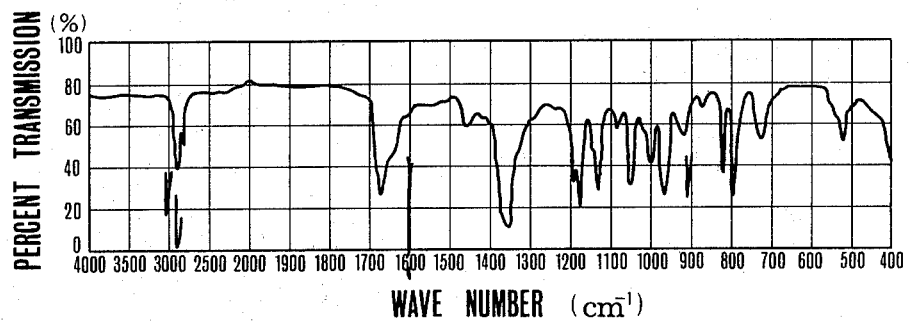

This invention relates to novel compounds of 2-cyclo-hexene-1-one-derivatives, to a process for the preparation thereof and their uses as selective herbicide.

More particularly, this invention is directed to compositions and methods employing, as an active herbicidal ingredient, at least one compound of the formula:

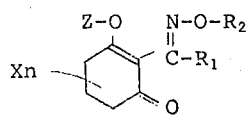  [I]

where
- $R_1$ is selected from the group consisting of phenyl and straight or branched chain alkyl;
- $R_2$ is selected from the group consisting of straight or branched chain lower alkyl, straight or branched chain lower alkenyl, lower alkynyl, lower alkoxymethyl, lower alkylthiomethyl and benzyl;
- X is a same or different substituent which is selected from the group consisting of straight or branched chain alkyl, lower alkoxycarbonyl, phenyl, substituted phenyl having at least one substituent selected from the group consisting of halogen, methyl and methoxy, styryl, furyl, thienyl and —$(CH_2)m$— in which $m$ is an integer from 1 to 6;
- $n$ is 0 or an integer from 1 to 6;
- Z is a substituent selected from the group consisting of R—A— and T in which R is selected from the group consisting of lower alkyl, phenyl, substituted phenyl having at least one substituent selected from the group consisting of halogen, methyl, methoxy and nitro, benzyl, phenoxymethyl and phenoxymethyl substituted with at least one halogen;
- A is selected from the group consisting of carbonyl and sulfonyl;
- T is selected from the group consisting of lower alkyl and benzyl.

Preferred for use according to this invention because they are effective as herbicides at lower rates of application are compounds of the formula

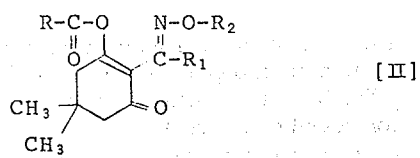  [II]

where:
- R is phenyl or substituted phenyl;
- $R_1$ is ethyl or propyl;
- $R_2$ is ethyl, propyl, allyl or propargyl.

Especially preferred for use because of their herbicidal effectiveness are:
2-(N-allyloxypropionimidoyl)-3-(4-chlorobenzoyloxy)-5,5-dimethyl-2-cyclohexene-1-one,
2-(N-allyloxybutyrimidoyl)-3-benzoyloxy-5,5-dimethyl-2-cyclo-hexene-1-one,
2-(N-allyloxypropionimidoyl)-3-(4-nitrobenzoyloxy)-5,5-dimethyl-2-cyclohexene-1-one, 2-(N-allyloxypropionimidoyl)-3-benzoyloxy-5,5-dimethyl-2-cyclohexene-1-one,
3-benzoyloxy-5,5-dimethyl-2-N-propargyloxybutyrimidoyl-2-cyclohexene-1-one,
2-(N-allyloxypropionimidoyl)-3-(3-methoxybenzoyloxy)-5,5-dimethyl-2-cyclohexene-1-one,
2-(N-allyloxypropionimidoyl)-3-(3-chlorobenzyloxy)-5,5-dimethyl-2-cyclohexene-1-one,
4-(4-methylbenzoyloxy)-5,5-dimethyl-2-(N-propargyloxybutyrimidoyl)-2-cyclohexene-1-one, The compounds of this invention can be prepared in accordance with the following equation:

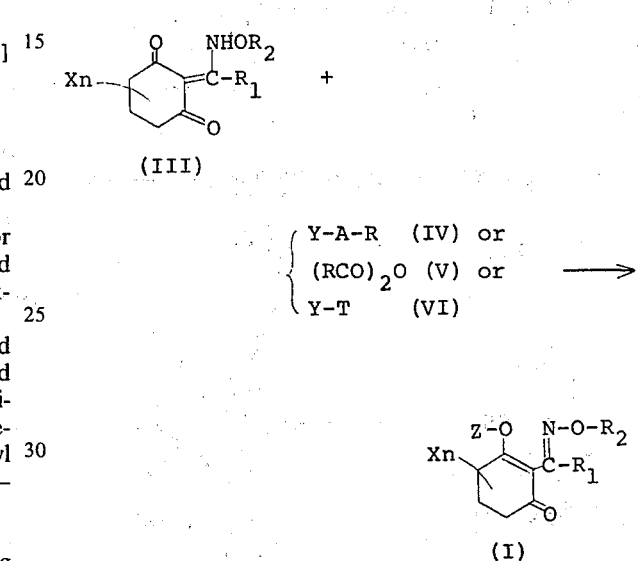

wherein $R_1$, $R_2$, R, X, $n$, A, T and Z are as previously defined and Y represents halogen atom.

The starting material (III) can be prepared in accordance with the following equation:

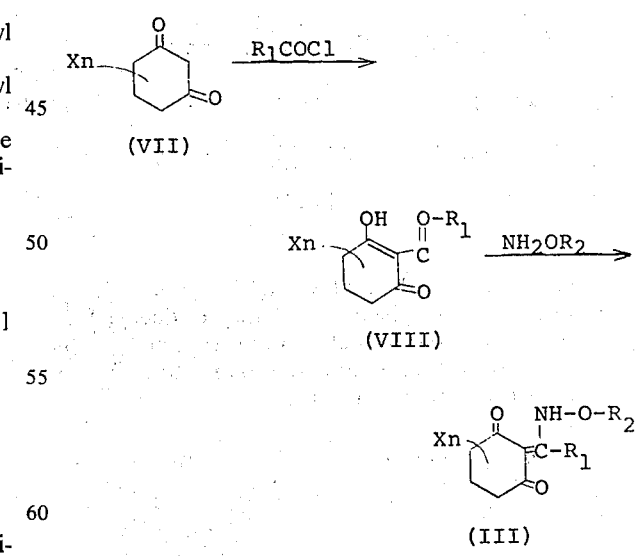

Almost all of the compounds having above formula (VII) are known and they can be prepared by methods heretofore described in the literature.

For example, methods for preparing above substituted cyclohexane-1,3-diones (VII) are illustrated by the following equations:

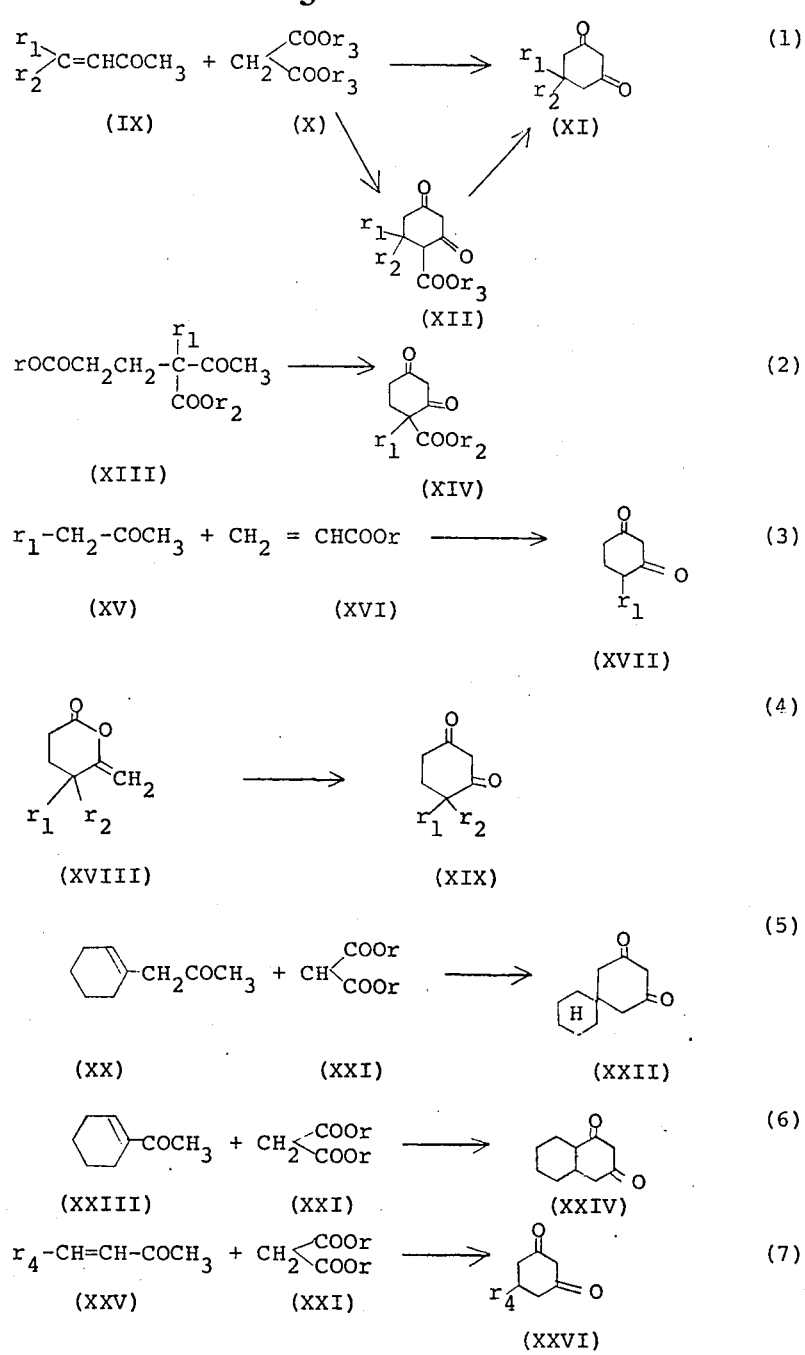

wherein $r_1$, $r_2$, $r_3$ and $r$ are lower alkyl, $r_4$ is lower alkyl, phenyl, substituted phenyl, styryl, furyl or thienyl. With respect to the above formula (III) it is expected that the said compound has the following three structural formulae because of tautomerism:

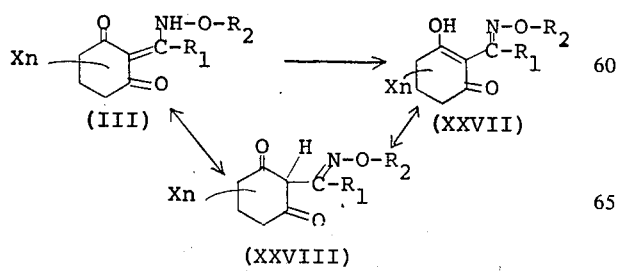

In practical method first of all an alkali metal salt of the starting compound (III) is prepared by treating it with sodium or potassium hydroxide in an aqueous solution or an organic solvent.

The said alkali metal salt is made to react with the compound of general formula (IV), (V) or (VI) in an inert solvent after separating it from the reaction mixture or as it is.

As an inert solvent, acetone, ether, alcohol, benzene, toluene, chloroform and a ethyl acetate etc. are used.

Ordinarily, temperatures from the range of −20° C to the boiling point of the solvent, and preferably below room temperature, are satisfactorily employed for the above reaction and the reaction terminates between about 15 minutes and 5 hours.

After finishing the reaction, the employed solvent, if necessary, is replaced with the other solvent and then, the reaction mixture is washed with alkaline solution and water and dried, and further, solvent is distilled under reduced pressure, thereby the crude product is obtained as crystal or liquid.

The crude product can be purified by recrystallization or colum chromatography. A structural formula of the resulting purified compound can be confirmatively identified by means of an elementary analysis, NMR spectrum or IR spectrum etc.

In order that the invention may be better understood, the following examples are given:

AN EXPLANATION OF THE DRAWING

Figure 2:
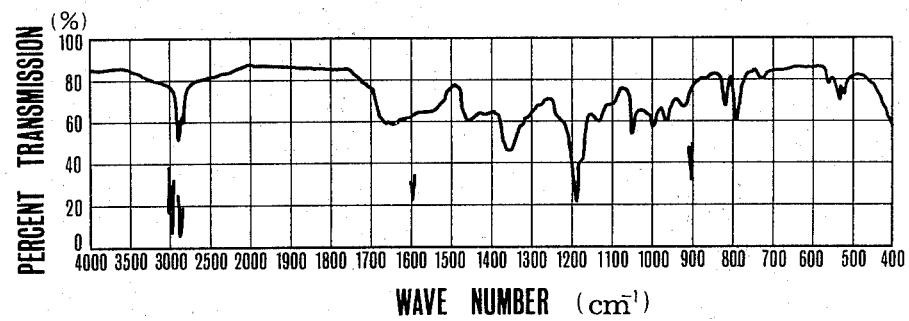
Figure 3:
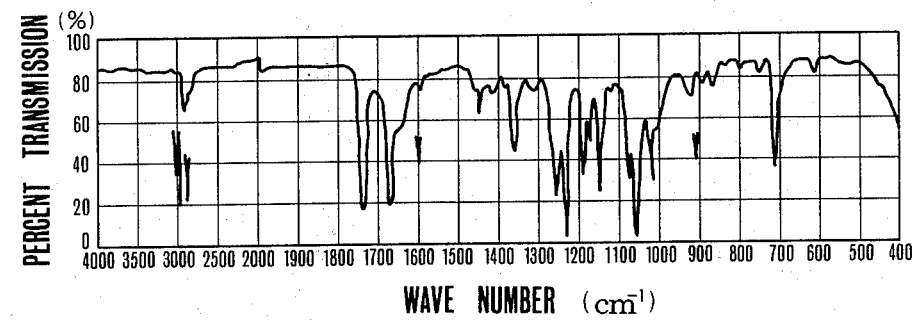
Figure 7:
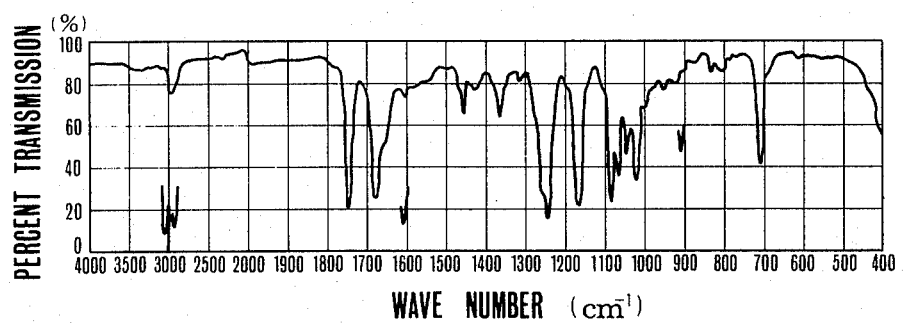
Figure 4:
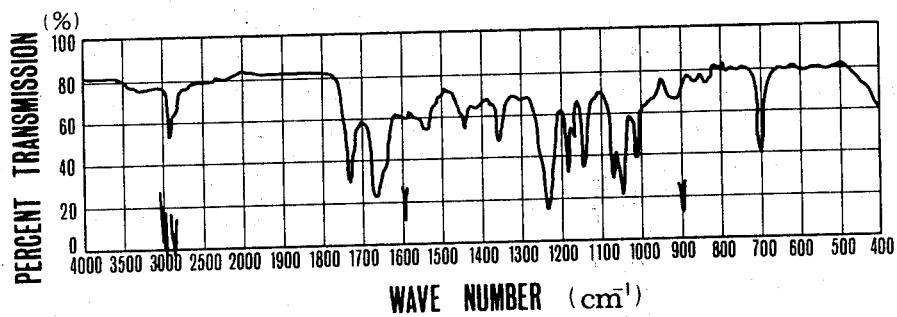
Figure 5:
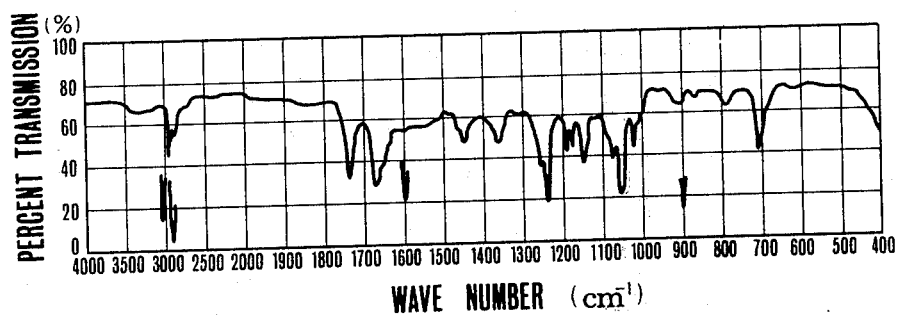
Figure 6:
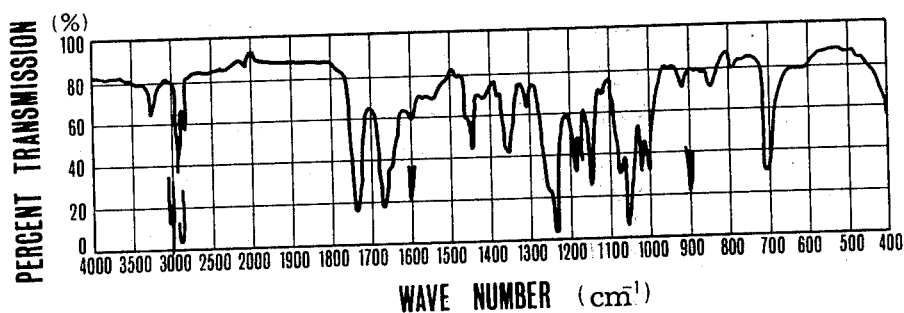

FIG. 1 is the infrared spectrum of Compound No. 1.
FIG. 2 is the infrared spectrum of Compound No. 2.
FIG. 3 is the infrared spectrum of Compound No. 5.
FIG. 4 is the infrared spectrum of Compound No. 8.
FIG. 5 is the infrared spectrum of Compound No. 14.
FIG. 6 is the infrared spectrum of Compound No. 16.
FIG. 7 is the infrared spectrum of Compound No. 38.

EXAMPLE 1

3-Benzoyloxy-2-(N-ethoxypropionimidoyl)-5,5-dimethyl-2-cyclohexene-1-one 2.4 g of 2-[1-(N-ethoxyamino)propylidene]-5,5-dimethylcyclohexane-1,3-dione were dissolved in 20ml of acetone of 2 ml of aqueous solution containing 0.4 g of dissolved sodium hydroxide was added in above resulting solution at room temperature with stirring. After cooling the resulting solution, 1.4 g of benzoyl chloride was added dropwise to it at a temperature range of −5° to 0° C and it was stirring for about 15 minutes. Further, the resulting solution was stirring for about 20 minutes at room temperature. After finishing the reaction, said acetone was distilled off under reduced pressure and the residual material was dissolved in 20 ml of chloroform.

The resulting chloroform layer was washed with 10 ml of aqueous solution containing 2% of sodium hydroxide and with 10 ml of water. The said chloroform layer was dried with magnesium sulfate. The chloroform solution was filtered and chloroform was distilled off under reduced pressure and thereby, 3-benzoyloxy-2-(N-ethoxypropionimidoyl)-5,5-dimethyl-2-cyclohexene-1-one was obtained as a colorless liquid.

Yield: 3.3 g (96%)
Refractive index: $n_D^{31}$:1.5269

EXAMPLE 2

3-(4-chlorobenzoyloxy)-2-(N-ethoxypropionimidoyl)-5,5-dimethyl-2-cyclohexene-1-one The same reaction procedures as Example 1 were carried out by using 2.4 g of 2-[1-(N-ethoxyamino)-propylidene]-5,5-dimethylcyclohexane-1,3-dione and 1.75 g of 4-chlorobenzoylchloride, and chloroform was distilled off under reduced pressure and thereby the desired product as a white crystal was obtained after recrystallization the residual material from n-hexane.

Yield: 3.5 g (93%)
Melting point: 60° – 62° C

EXAMPLE 3

The following compounds (C) can be synthesized by the method of Example 1 substituting the appropriate substituted cyclohexane 1,3-dione (A) for 2-[1-(N-ethoxyamino)propylidene]-5,5-dimethylcyclohexane-1,3-dione and the appropriate acyl halide or sulfonyl halogenide (B) for benzoyl chloride.

Compound No. 2

A. 2[1-(N-allyloxyamino)hexylidene]-5,5-dimethyl-cyclohexane-1,3-dione, 2.9 g
B. methanesufonylchloride, 1.5 g
C. 2-(N-allyloxyhexaneimidoyl)-5,5-dimethyl-3-methonesulfonyloxy2-(cyclohexene-1-one, colorless liquid
Yield: 3.2 g (87%)
Refractive index: $n_D^{31}$:1.4960

Compound No. 18

A. 2-[1-(N-allyloxyamino)benzylidene]-5,5-dimethylcyclohexane-1,3-dione, 3.0 g
B. benzoyl chloride, 1.4 g
C. 2-(N-allyloxybenzimidoyl)-3-benzoyloxy-5,5-dimethyl-2-cyclohexene-1-one, light yellow liquid
Yield: 3.3 g (93%)
Refractive index: $n_D^{19.5}$:1.5770

Compound No. 29

A. 2-[1-(N-ethoxyamino)propylidene]-5,5-dimethyl-cyclohexane-1,3-dione, 2.4 g
B. 4-methyl-benzoylchloride, 1.5 g
C. 2-(N-ethoxypropionimidoyl)-3-(4-methylbenzoyloxy)-5,5-dimethyl-3-cylohexene-1-one, yellow liquid
Yield: 3.2 g (90%)
Refractive index: $n_D^{31}$:1.5139

Compound No. 31

A. 2-[1-(N-ethoxyamino)hexylidene]-5,5-dimethyl-cyclohexane-1,3-dione, 2.8 g
B. tosylchloride, 1.9 g
C. 2-(N-ethoxyhexaneimidoyl)-3-tosyloxy-5,5-dimethyl-2-cyclohexene-1-one, colorless liquid
Yield: 4.2 g (92%)
Refractive index: $n_D^{31}$:1.5215

Compound No. 33

A. 2-[1-(N-allyloxyamino)butylidene]-5,5-dimethyl-cyclohexane-1,3-dione, 2.65 g
B. 3-methoxybenzoylchloride, 1.7 g
C. 2-(N-allyloxybutyrimidoyl)-3-(2-methoxybenzoyloxy)-5,5-dimethyl-2-cyclohexene-1-one, yellow liquid
Yield: 3.8 g (95%)
Refractive index: $n_D^{31}$:1.5363

Compound No. 38

A. 2-[1-(N-allyloxyamino)propylidene]-cyclohexane-1,3-dione, 2.2 g
B. benzoylchloride, 1.4 g
C. 2-(N-allyloxypropionimidoyl)-3-benzoyloxy-3-cyclohexene-1-one, colorless liquid
Yield: 3.1 g (95%)
Refractive index: $n_D^{26}$:1.5479

Compound No. 39

A. 2-[1-(N-allyloxyamino)propylidene]-5-methylcyclohexane-1,3-dione, 2.4 g
B. benzoylchloride, 1.4 g
C. 2-(N-allyloxypropionimidoyl)-3-benzoyloxy-5-methyl-2-cyclohexene-1-one, orange liquid
Yield: 3.3 g (97%)
Refractive index: $n_D^{20}$:1.5362

Compound No. 43

A. 2-[1-(N-ethoxyamino)propylidene]-5-hexylcyclohexane-1,3-dione, 2.95 g
B. benzenesulfonyl chloride, 1.7 g
C. 2-(N-ethoxypropionimidoyl)-3-phenylsulfonyloxy-5-hexyl-2-cyclohexene-1-one, light yellow liquid
Yield: 4.1 g (94%)
Refractive index: $n_D^{18}$:1.5221

Compound No. 44

A. 2-[1-(N-allyloxyamino)propylidene]-5-phenylcyclohexane-1,3-dione, 3.0 g
B. benzoylchloride, 1.4 g
C. 2-(N-allyloxypropionimidoyl)-3-benzoyloxy-5-phenyl-2-cyclohexene-1-one, light yellow liquid
Yield: 3.7 g (92%)
Refractive index: $n_D^{19.5}$:1.5775

EXAMPLE 4

The following compounds (C) can be synthesized by the method of Example 2 substituting the appropriate substituted cyclohexane-1,3-dione (A) for 2-[1-(N-ethoxyamino)propylidene]-5,5-dimethylcyclohexane-1,3-dione and the appropriate acyl halide or sulfonyl halogenide (B) for benzoyl chloride.

Compound No. 36

A. 2-[1-(N-allyloxyamino)propylidene]-5,5-dimethylcyclohexane-1,3-dione, 2.5 g
B. 4-nitrobenzoyl chloride, 1.85 g
C. 2-(N-allyloxypropionimidoyl)-5,5-dimethyl-3-(4-nitrobenzoyloxy)-2-cyclohexene-1-one, white crystal
Yield: 3.8 g (95%)
Melting point: 78° – 80° C

Compound No. 12

A. 2-[1-(N-benzyloxyamino)propylidene]-5,5-dimethylcyclohexane-1,3-dione, 3.0 g
B. benzoyl chloride, 1.4 g
C. 2-(N-benzyloxypropionimidoyl)-3-benzoyloxy-5,5-dimethyl-2-cyclohexene-1-one, white crystal
Yield: 3.8 g (95%)
Melting point: 54° – 55° C

EXAMPLE 5

2-(N-allyloxybutyrimidoyl)-5,5-dimethyl-3-propionyloxy-2-cyclohexene-1-one 5.4 g of 2-[1-(N-allyloxyamino)butylidene]-5,5-dimethylcyclohexane-1,3-dione were dissolved in 40 ml of acetone and 4 ml of aqueous solution containing 0.8 g of dissolved sodium hydroxide were added in above resulting solution at room temperature with stirring. Dried sodium metal salt of 2-[1-(N-allyloxyamino) butylidene]-5,5-dimethylcyclohexane-1,3-dione was obtained by distillating acetone under reduced pressure. 40 ml of dried acetone were added to said sodium salt and 1.8 g of propionyl chloride was added dropwise to the resulting solution at a temperature range of −5° to 0° C after cooling it. After stirring the resulting solution for about 30 minutes, acetone was distilled under reduced pressure and the residual material was dissolved in 40 ml of ether. Then, the resulting ether layer was dried with magnesium solfate after washing it with 20 ml of aqueous solution containing 2% of sodium hydroxide and 20 ml of water. The said ether solution was filtered and 2-(N-allyloxybutyrimidoyl)-5,5-dimethyl-3-propionyloxy-2-cyclohexene-1-one was obtained as a colorless liquid by distillating ether under reduced pressure.
Yield: 5.2 g (80%)
Refractive index: $n_D^{31}$:1.4762

EXAMPLE 6

3-Benzoyloxy-2-(N-ethoxybutyrimidoyl)-5,5-dimethyl-6-methoxycarbonyl-2-cyclohexene-1-one To a solution of 5,5-dimethyl-2-(N-ethoxyaminobutylidene)-4-methoxycarbonylcyclohexane-1,3-dione (3.1g) in 30 ml of acetone, 1 ml of aqueous solution containing 0.4 g of dissolved sodium hydroxide was added at room temperature and then benzoyl chloride (1.4g) was added. After stirring for 5 hours, the reaction mixture was poured into ice-water and extracted with chloroform. The extract was washed with one normal sodium hydroxide and dried over magnesium sulfate. The solvent was removed in vacuo and the desired product as an oily substance was obtained.
Yield: 2.8 g
Refractive index: $n_D^{24.5}$:1.5165

EXAMPLE 7

The following compound (C) can be synthesized by the method of Example 6 substituting the appropriate substituted cyclohexane-1,3-dione (A) for 5,5-dimethyl-2-(N-allyloxyaminobutylidene)-4-methoxycarbonylcyclohexane-1,3-dione and the appropriate acyl halide or sulfonyl halogenide (B) for benzoyl chloride.

Compound No. 105

A. 2-(1-allyloxyaminopropylidene)-4-ethoxycarbonyl-4-ethylcyclohexane-1,3-dione, 1.6 g
B. benzoyl chloride, 0.7 g
C. 2-(N-allyloxypropionimidoyl)-3-benzyloxy-6-ethoxycarbonyl-6-ethyl-2-cyclohexene-1-one
Yield: 1.3 g
Refractive index: $n_D^{24}$ 1.5225

Compound No. 84

A. 2-(1-allyloxyaminopropylidene)-5,5-dimethyl-4-ethoxycarbonyl-cyclohexane-1,3-dione, 3.2 g
B. 4-chlorobenzoyl chloride, 1.7 g
C. 2-(N-allyloxypropionimidoyl)-3-(4-chlorobenzoyloxy)-6-ethoxycarbonyl-5,5-dimethyl-2-cyclohexene-1-one,
Yield: 2.3 g
Refractive index: $n_D^{22}$ 1.5348

Compound No. 117

A. 2-(1-allyloxyaminopropylidene)-5-styrylcyclohexane-1,3-dione, 3.3 g
B. benzoyl chloride, 1.4 g
C. 2-(N-allyloxypropionimidoyl)-3-benzoyloxy-5-styryl-2-cyclohexene-1-one
Yield: 1.5 g
Refractive index: $n_D^{25}$ 1.5857

Compound No. 118

A. 2-(1-ethoxyaminopropylidene)-5-(2-furyl)cyclohexane-1,3-dione, 1.4 g
B. benzoyl chloride, 0.7 g
C. 3-benzoyloxy-2-(N-ethoxypropionimidoyl)-5-(2-furyl)-2-cyclohexene-1-one,
Yield: 1.6 g Refractive index: $n_D^{19}$ 1.5546

Compound No. 107

A.  5-(4-chlorophenyl)-2-(1-ethoxyaminopropylidene)-cyclohexane-1,3-dione, 1 g
B.  benzoyl chloride, 0.42 g
C.  3-benzoyloxy-5-(4-chlorophenyl)-2-(N-ethoxypropionimidoyl)-2-cyclohexene-1-one
Yield: 1.2 g
Refractive index: $n_D^{24.5}$ 1.5720

Compound No. 120

A.  2-(1-allyloxyaminopropylidene)-5,5-dimethylcyclohexane-1,3-dione, 2.5 g
B.  phenylacetyl chloride, 1.5 g
C.  2-(N-allyloxypropionimidoyl)-5,5-dimethyl-3-phenylacetoxy-2-cyclohexene-1-one
Yield: 1.8 g
Refractive index: $n_D^{22}$ 1.5249

Compound No. 122

A.  2-(1-ethoxyaminopropylidene)-4-isobutylcyclohexane-1,3-dione, 1.3 g
B.  phenylacetyl chloride, 0.8 g
C.  2-(N-ethoxypropionimidoyl)-6-isobutyl-3-phenylacetoxy-2-cyclohexene-1-one
Yield: 0.4 g
Refractive index: $n_D^{24}$ 1.5172

Compound No. 125

A.  5,5-dimethyl-2-(1-methylthiomethoxyaminopropylidene)-cyclohexane-1,3-dione, 1.4 g
B.  benzoyl chloride, 0.7 g
C.  3-benzoyloxy-5,5-dimethyl-2-(N-methylthiomethoxypropionimidoyl)-2-cyclohexene-1-one
Yield: 1.2 g
Refractive index: $n_D^{25}$ 1.5415

Compound No. 127

A.  5-isopropyl-2-(1-methylthiomethyloxyaminopropylidene)-cyclohexane-1,3-dione, 1.4 g
B.  benzoyl chloride, 0.7 g
C.  3-benzoyloxy-5-isopropyl-2-(N-methylthiomethyloxypropionimidoyl)-2-cyclohexene-1-one
Yield: 1.7 g
Refractive index: $n_D^{23}$ 1.5495

Compound No. 130

A.  2-(1-butoxymethyloxyaminopropylidene)-5,5-dimethylcyclohexane-1,3-dione, 2 g
B.  methylsulfonyl chloride, 0.7 g
C.  2-(N-butoxymethyloxypropionimidoyl)-5,5-dimethyl-3-methylsulfonyloxy-2-cyclohexene-1-one
Yield: 1.1 g
Refractive index: $n_D^{23}$ 1.4885

EXAMPLE 8

5-(2,4-Dichlorophenyl)-2-(N-ethoxypropionimidoyl)-3-methylsulfonyloxy-2-cyclohexene-1-one To a solution of 5-(2,4-dichlorophenyl)-2-(1-ethopyaminopropylidene)-cyclohexane-1,3-dione (1.4 g) in acetone (30 ml), sodium hydroxide (0.2 g) in water (2 ml) was added at room temperature and then methanesulfonyl chloride (0.5 g) was added. After stirring for 1 hr, the reaction mixture was poured into ice-water and extracted with chloroform. The extract was washed with one normal sodium hydroxide and dried over magnesium sulfate. The solvent was removed in vacuo and an oily substance (0.5 g) was obtained. The desired product having a melting point of 73° to 75° C was obtained as colorless prisms by recrystallizing said oily substance from n-hexane.

EXAMPLE 9

The following compound (C) can be synthesized by the method of Example 8 substituting the appropriate substituted cyclohexane-1,3-dione (A) for 5-(2,4-dichlorophenyl)-2-(1-ethoxyaminopropylidene) cyclohexane-1,3-dione and the appropriate acyl halide or sulfonyl halogenide (B) for methanesulfonyl chloride.

Compound No. 135

A.  2-(1-allyloxyaminopropylidene)-5,5-dimethylcyclohexane-1,3-dione, 2.5 g
B.  benzoyl chloride, 2.1 g
C.  2-(N-allyloxypropionimidoyl)-3-(2,4-dichlorobenzoyloxy)-5,5-dimethyl-2-cyclohexene-1-one, colorless crystal
Melting point: 74° – 75° C

Compound No. 136

A.  5,5-dimethyl-2-(1-propargyloxyaminobutylidene)cyclohexane-1,3-dione, 2.5 g
B.  3,6-dichloro-2-methoxybenzoylchloride, 2.2 g
C.  3-(3,6-dichloro-2-methoxybenzoyloxy)-5,5-dimethyl-2-(N-propargyloxybutyrimidoyl)-2-cyclohexene-1-one, colorless crystal,
Melting point: 87° – 88° C

EXAMPLE 10

3-Acetoxy-6-ethoxycarbonyl-2-(N-ethoxypropionimidoyl)-2-cyclohexene-1-one

Sodium salt of 2-(1-ethoxyaminopropylidene)-4-ethoxycarbonyl-5,5-dimethylcyclohexane-1,3-dione (3.1 g) was suspended in 50 ml of acetone and acetylchloride (0.8 g) was added to it at room temperature. After stirring for 3 hours, the reaction mixture was poured into ice-water and extracted with chloroform. The extract was washed with one normal sodium hydroxide and dried over magnesium sulfate. The solvent was removed is vacuo and the desired product was obtained as an oily substance.
Yield: 1.2 g
Refractive index: $n_D^{18}$ 1.4848

EXAMPLE 11

2-(N-allyloxybutyrimidoyl)-5,5-dimethyl-3-methoxy-2-cyclohexene-1-one

Silver salt of 2-(1-allyloxyaminobutylidene)-5,5-dimethylcyclohexane-1,3-dione (25 g) was suspended in 100 ml of ether and methyl iodide (34 g) was added. The mixture was refluxed for 6 hours with stirring. After filtering silver iodide, the solvent was removed in vacuo and then poured into water. The oil thus separated was extracted with chloroform and washed with one normal sodium hydroxide and dried over magnesium sulfate. The solvent was removed in vacuo and the desired product was obtained as an oily substance.
Yield: 11.5 g
Refractive index: $n_D^{26}$ 1.3532

EXAMPLE 12

2-(N-allyloxypropionimidoyl)-3-benzyloxy-5,5-dimethyl-2-cyclohexene-1-one

To a solution of 2-(1-allyloxyaminopropylidene)-5,5-dimethylcyclohexane-1,3-dione (2.5 g) in acetone (30 ml), sodium hydroxide (0.4 g) in water (2 ml) was added at room temperature and then benzyl bromide (2.0 g) was added. After stirring for 10 hours at 60° C the reaction mixture was poured into ice-water and extracted with chloroform. The extract was washed with one normal sodium hydroxide and dried over magnesium sulfate. The solvent was removed in vacuo and an oily substance which solidified on standing at 0° C was obtained. Recrystallization from the mixture of methanol and water gave the desired product as crystal.

Melting point: 60.5° – 61.5° C

EXAMPLE 13

7-(N-allyloxypropionimidoyl)-6-benzoyloxy-1,2,3,4,5,8,4a,8a-octahydronaphthalene-8-one To a solution of 2-(1-allyloxyaminopropylidene)-decaline-1,3-dione (2 g) in acetone (30 ml), sodium hydroxide (0.2 g) in water (1 ml) was added at room temperature and then benzoylchloride (0.7 g) was added. After stirring for 5 hours, the reaction mixture was poured into ice-water and extracted with chloroform. The extract was washed with one normal sodium hydroxide and dried over magnesium sulfate. The solvent was removed in vacuo and an oily substance (1.8 g) was obtained.

Refractive index: $n_D^{20.5}$ 1.5499 (Another nomenclature of Compound No. 133)

EXAMPLE 14

4-(N-allyloxypropionimidoyl)-3-benzoyloxy-5-oxo-3-cyclohexenespirocyclohexane

To a solution of 4-(1-allyloxyaminopropylidene)-spirobicyclohexane-3,5-dione (1.5 g) in acetone (30 ml), sodium hydroxide (0.2 g) in water (1 ml) was added at room temperature and then benzoylochloride (0.7 g) was added. After stirring for 5 hr, the reaction mixture was poured into ice-water and extracted with chloroform. The extract was washed with one normal sodium hydroxide and dried over magnesium sulfate. The solvent was removed in vacuo and oily substance (0.8 g) was obtained.

Refractive index: $n_D^{23}$ 1.5475 (Another nomenclature of Compound No. 134)

In addition to the above mentioned compounds described in the preceding example, some typical compounds of the present invention are listed in Table 1.

Table 1

| Compound No. | Chemical Name | Physical constant |
|---|---|---|
| 1 | 2-(N-ethoxybutyrimidoyl)-3-methylsulfonyloxy-5,5-dimethyl-2-cyclohexene-1-one | $n_D^{31}$1.4896 |
| 2 | 2-(N-allyloxyhexanimidoyl)-3-methylsulfonyloxy-5,5-dimethyl-2-cyclohexene-1-one | $n_D^{31}$1.4960 |
| 3 | 2-(N-allyloxybutyrimidoyl)-3-propionyloxy-5,5-dimethyl-2-cyclohexene-1-one | $n_D^{31}$1.4762 |
| 4 | 2-(N-ethoxypropionimidoyl)-3-ethylsulfonyloxy-5,5-dimethyl-2-cyclohexene-1-one | $n_D^{29.5}$1.4874 |
| 5 | 2-(N-allyloxyacetimidoyl)-3-benzoyloxy-5,5-dimethyl-2-cyclohexene-1-one | $n_D^{31}$1.5289 |
| 6 | 2-(N-ethoxypropionimidoyl)-3-benzoyloxy-5,5-dimethyl-2-cyclohexene-1-one | $n_D^{31}$1.5269 |
| 7 | 2-(N-propoxypropionimidoyl)-3-benzoyloxy-5,5-dimethyl-2-cyclohexene-1-one | $n_D^{24.5}$1.5350 |
| 8 | 2-(N-allyloxypropionimidoyl)-3-benzoyloxy-5,5-dimethyl-2-cyclohexene-1-one | $n_D^{29}$1.5338 |
| 9 | 2-(N-propargyloxypropionimidoyl)-3-benzoyloxy-5,5-dimethyl-2-cyclohexene-1-one | $n_D^{18.5}$1.5401 |
| 10 | 2-(N-butoxypropionimidoyl)-3-benzoyloxy-5,5-dimethyl-2-cyclohexene-1-one | $n_D^{18.5}$1.5249 |
| 11 | 2-(N-isobutoxypropionimidoyl)-3-benzoyloxy-5,5-dimethyl-2-cyclohexene-1-one | d.p.: 64 to 64° C |
| 12 | 2-(N-benzyloxypropionimidoyl)-3-benzoyloxy-5,5-dimethyl-2-cyclohexene-1-one | m.p.: 54 to 55° C |
| 13 | 2-(N-methoxybutyrimidoyl)-3-benzoyloxy-5,5-dimethyl-2-cyclohexene-1-one | $n_D^{23}$1.5291 |
| 14 | 2-(N-ethoxybutyrimidoyl)-3-benzoyloxy-5,5-dimethyl-2-cyclohexene-1-one | $n_D^{31}$1.5090 |
| 15 | 2-(N-allyloxybutyrimidoyl)-3-benzoyloxy-5,5-dimethyl-2-cyclohexene-1-one | $n_D^{31}$1.5274 |
| 16 | 2-(N-propargyloxybutyrimidoyl)-3-benzoyloxy-5,5-dimethyl-2-cyclohexene-1-one | $n_D^{31}$1.5370 |
| 17 | 2-(N-ethoxyisobutyrimidoyl)-3-benzoyloxy-5,5-dimethyl-2-cyclohexene-1-one | $n_D^{23}$1.5228 |
| 18 | 2-(N-allyloxybenzimidoyl)-3-benzoyloxy-5,5-dimethyl-2-cyclohexene-1-one | $n_D^{19.5}$1.5770 |
| 19 | 2-(N-ethoxypropionimidoyl)-3-phenylsulfonylloxy-5,5-dimethyl-2-cyclohexene-1-one | $n_D^{31}$1.5259 |
| 20 | 2-(N-allyloxyacetimidoyl)-3-(4-chlorobenzoyloxy)-5,5-dimethyl-2-cyclohexene-1-one | $n_D^{31}$1.5371 |
| 21 | 2-(N-ethoxypropionimidoyl)-3-(4-chlorobenzoyloxy)-5,5-dimethyl-2-cyclohexene-1-one | m.p.: 60 to 62° C |
| 22 | 2-(N-allyloxypropionimidoyl)-3-(4-chlorobenzoyloxy)-5,5-dimethyl-2-cyclohexene-1-one | m.p.: 53 to 54° C |
| 23 | 2-(N-ethoxybutyrimidoyl)-3-(4-chlorobenzoyloxy)-5,5-dimethyl-2-cyclohexene-1-one | $n_D^{31}$1.5295 |
| 24 | 2-(N-isopropoxybutyrimidoyl)-3-(4-chlorobenzoyloxy)-5,5-dimethyl-2-cyclohexene-1-one | $n_D^{31}$1.5252 |
| 25 | 2-(N-ethoxyhexanimidoyl)-3-(4-chlorobenzoyloxy)-5,5-dimethyl-2-cyclohexene-1-one | $n_D^{31}$1.5205 |
| 26 | 2-(N-allyloxypropionimidoyl)-3-(4-chlorophenylsulfonyloxy)-5,5-dimethyl-2-cyclohexene-1-one | $n_D^{31}$1.5366 |
| 27 | 2-(N-methoxybutyrimidoyl)-3-(4-chlorophenylsulfonyloxy)-5,5-dimethyl-2-cyclohexene-1-one | $n_D^{23}$1.5362 |
| 28 | 2-(N-ethoxyhexanimidoyl)-3-(4-chlorophenylsulfonyloxy)-5,5-dimethyl-2-cyclohexene-1-one | $n_D^{31}$1.5248 |
| 29 | 2-(N-ethoxypropionimidoyl)-3-(4-methylbenzoyloxy)-5,5-dimethyl-2-cyclohexene-1-one | $n_D^{31}$1.5139 |
| 30 | 2-(N-ethoxybutyrimidoyl)-3-(4-methylbenzoyloxy)-5,5-dimethyl-2-cyclohexene-1-one | $n_D^{31}$1.5212 |
| 31 | 2-(N-ethoxyhexanimidoyl)-3-tosyloxy-5,5-dimethyl-2-cyclohexene-1-one | $n_D^{31}$1.5215 |
| | 2-(N-isopropoxybutyrimidoyl)- | |

Table 1-continued

| Compound No. | Chemical Name | Physical constant |
|---|---|---|
| 32 | 3-tosyloxy-5,5-dimethyl-2-cyclohexene-1-one | $n_D^{31}1.5192$ |
| 33 | 2-(N-allyloxybutyrimidoyl)-3-(2-methoxybenzoyloxy)-5,5-dimethyl-2-cyclohexene-1-one | $n_D^{31}1.5363$ |
| 34 | 2-(N-allyloxyhexanimidoyl)-3-(2-methoxybenzoyloxy)-5,5-dimethyl-2-cyclohexene-1-one | $n_D^{30}1.5264$ |
| 35 | 2-(N-allyloxypropionimidoyl)-3-(3-methoxybenzoyloxy)-5,5-dimethyl-2-cyclohexene-1-one | $n_D^{31}1.5294$ |
| 36 | 2-(N-allyloxypropionimidoyl)-3-(4-nitrobenzoyloxy)-5,5-dimethyl-2-cyclohexene-1-one | m.p.: 78 to 80° C |
| 37 | 2-(N-propoxypropionimidoyl)-3-(4-nitrophenylsulfonyloxy)-5,5-dimethyl-2-cyclohexene-1-one | $n_D^{24.5}1.5375$ |
| 38 | 2-(N-allyloxypropionimidoyl)-3-benzoyloxy-2-cyclohexene-1-one | $n_D^{26}1.5479$ |
| 39 | 2-(N-allyloxypropionimidoyl)-3-benzoyloxy-5-methyl-2-cyclohexene-1-one | $n_D^{20}1.5362$ |
| 40 | 2-(N-ethoxyacetimidoyl)-3-benzoyloxy-5-methyl-2-cyclohexene-1-one | $n_D^{18.5}1.5389$ |
| 41 | 2-(N-allyloxypropionimidoyl)-3-methylsulfonyloxy-5-hexyl-2-cyclohexene-1-one | $n_D^{18}1.4987$ |
| 42 | 2-(N-ethoxybutyrimidoyl)-3-benzoyloxy-5-hexyl-2-cyclohexene-1-one | $n_D^{18.5}1.5209$ |
| 43 | 2-(N-ethoxypropionimidoyl)-3-phenylsulfonyloxy-5-hexyl-2-cyclohexene-1-one | $n_D^{18}1.5221$ |
| 44 | 2-(N-allyloxypropionimidoyl)-3-benzoyloxy-5-phenyl-2-cyclohexene-1-one | $n_D^{19.5}1.5775$ |
| 45 | 2-(N-allyloxypropionimidoyl)-3-(4-methylbenzoyloxy)-5,5-dimethyl-2-cyclohexene-1-one | m.p.: 46 to 47° C |
| 46 | 2-(N-allyloxypropionimidoyl)-3-(3-methoxybenzoyloxy)-5,5-dimethyl-2-cyclohexene-1-one | m.p.: 46 to 47° C |
| 47 | 2-(N-allyloxypropionimidoyl)-3-(2-methoxybenzoyloxy)-5,5-dimethyl-2-cyclohexene-1-one | $n_D^{22}1.5371$ |
| 48 | 2-(N-allyloxypropionimidoyl)-3-(3-nitrobenzoyloxy)-5,5-dimethyl-2-cyclohexene-1-one | m.p.: 76 to 78° C |
| 49 | 2-(N-allyloxypropionimidoyl)-3-(2-methylbenzoyloxy)-5,5-dimethyl-2-cyclohexene-1-one | m.p.: 37 to 38° C |
| 50 | 2-(N-allyloxypropionimidoyl)-3-phenylsulfonyloxy-5,5-dimethyl-2-cyclohexene-1-one | $n_D^{22}1.5327$ |
| 51 | 2-(N-allyloxypropionimidoyl)-3-(4-phenylsulfonyloxy)-5,5-dimethyl-2-cyclohexene-1-one | $n_D^{22}1.5310$ |
| 52 | 2-(N-allyloxypropionimidoyl)-3-(3-chlorobenzoyloxy)-5,5-dimethyl-2-cyclohexene-1-one | m.p.: 39 to 40° C |
| 53 | 2-(N-propargyloxybutyrimidoyl)-3-(4-chlorobenzoyloxy)-5,5-dimethyl-2-cyclohexene-1-one | m.p.: 87 to 88° C |
| 54 | 2-(N-propargyloxybutyrimidoyl)-3-ethylsulfonyloxy-5,5-dimethyl-2-cyclohexene-1-one | $n_D^{19}1.5046$ |
| 55 | 2-(N-propargyloxybutyrimidoyl)-3-methylsulfonyloxy-5,5-dimethyl-2-cyclohexene-1-one | $n_D^{19}1.5101$ |
| 56 | 2-(N-propargyloxybutyrimidoyl)-3-(4-nitrobenzoyloxy)-5,5-dimethyl-2-cyclohexene-1-one | m.p.: 88 to 89° C |
| 57 | 2-(N-allyloxypropionimidoyl)-3-benzoyloxy-5-isopropyl-2-cyclohexene-1-one | $n_D^{19}1.5300$ |
| 58 | 2-(N-propargyloxybutyrimidoyl)-3-(3-nitrobenzoyloxy)-5,5-dimethyl-2-cyclohexene-1-one | $n_D^{19}1.5468$ |
| 59 | 2-(N-propargyloxybutyrimidoyl)-3-(4-methylbenzoyloxy)-5,5-dimethyl-2-cyclohexene-1-one | m.p.: 67 to 69° C |
| 60 | 2-(N-allyloxypropionimidoyl)-3-ethylsulfonyloxy-5,5-dimethyl-2-cyclohexene-1-one | $n_D^{19}1.5016$ |
| 61 | 2-(N-allyloxypropionimidoyl)-3-methylsulfonyloxy-5,5-dimethyl-2-cyclohexene-1-one | $n_D^{19}1.5020$ |
| 62 | 2-(N-allyloxypropionimidoyl)-3-benzoyloxy-5,5,6-trimethyl-2-cyclohexene-1-one | $n_D^{23}1.5341$ |
| 63 | 2-(N-ethoxypropionimidoyl)-3-(2-nitro-benzoyloxy)-6-isobutyl-2-cyclohexene-1-one | $n_D^{24}1.5345$ |
| 64 | 2-(N-allyloxypropionimidoyl)-3-benzoyloxy-6-propyl-2-cyclohexene-1-one | $n_D^{19}1.5328$ |
| 65 | 2-(N-ethoxypropionimidoyl)-3-phenylsulfonyloxy-6,6-dimethyl-2-cyclohexene-1-one | $n_D^{19}1.5292$ |
| 66 | 2-(N-ethoxypropionimidoyl)-3-(4-chlorobenzoyloxy)-6,6-dimethyl-2-cyclohexene-1-one | $n_D^{20}1.5372$ |
| 67 | 2-(N-ethoxypropionimidoyl)-3-methylsulfonyloxy-6,6-dimethyl-2-cyclohexene-1-one | $n_D^{20}1.4960$ |
| 68 | 2-(N-allyloxypropionimidoyl)-3-propionyloxy-6,6-dimethyl-2-cyclohexene-1-one | $n_D^{20}1.4918$ |
| 69 | 2-(N-allyloxypropionimidoyl)-3-benzoyloxy-6,6-dimethyl-2-cyclohexene-1-one | $n_D^{20}1.5357$ |
| 70 | 2-(N-allyloxypropionimidoyl)-3-(4-methylbenzoyloxy)-6-butyl-2-cyclohexene-1-one | $n_D^{24}1.5298$ |
| 71 | 2-(N-methallyloxypropionimidoyl)-3-methylsulfonyloxy-5,5-dimethyl-2-cyclohexene-1-one | $n_D^{23}1.5031$ |
| 72 | 2-(N-methallyloxypropionimidoyl)-3-benzoyloxy-5,5-dimethyl-2-cyclohexene | $n_D^{23}1.5293$ |
| 73 | 2-(N-ethoxybutyrimidoyl)-3-benzoyloxy-5-methyl-5-phenyl-2-cyclohexene-1-one | $n_D^{27.5}1.5598$ |
| 74 | 2-(N-ethoxybutyrimidoyl)-3-methylsulfonyloxy-5-methyl-5-phenyl-2-cyclohexene-1-one | $n_D^{27.5}1.5355$ |
| 75 | 2-(N-ethoxypropionimidoyl)-3-benzoyloxy-5-propyl-2-cyclohexene-1-one | $n_D^{27.5}1.5218$ |
| 76 | 2-(N-allyloxypropionimidoyl)-3-(2-chlorobenzoyloxy)-5,5-dimethyl-2-cyclohexene-1-one | $n_D^{29}1.5338$ |
| 77 | 2-(N-allyloxybutyrimidoyl)-3-(2-chlorobenzoyloxy)-5,5-dimethyl-2-cyclohexene-1-one | $n_D^{31}1.5269$ |
| 78 | 2-(N-ethoxybutyrimidoyl)-3-methylsulfonyloxy-5-methyl-5-phenyl-2-cyclohexene-1-one | $n_D^{27.5}1.5355$ |
| 79 | 2-(N-ethoxybutyrimidoyl)-3-benzoyloxy-5-methyl-5-phenyl-2-cyclohexene-1-one | $n_D^{27.5}1.5598$ |
| 80 | 2-(N-ethoxypropionimidoyl)-3-acetoxy-5,5-dimethyl-6-ethoxycarbonyl-2-cyclohexene-1-one | $n_D^{18}1.4848$ |
| 81 | 2-(N-ethoxypropionimidoyl)-3-benzoyloxy-5,5-dimethyl-6-ethoxycarbonyl-2-cyclohexene-1-one | $n_D^{18}1.5246$ |
| 82 | 2-(N-ethoxypropionimidoyl)-3-(4-chlorobenzoyloxy)-5,5-dimethyl-6-ethoxycarbonyl-2-cyclohexene-1-one | $n_D^{18}1.5282$ |
| 83 | 2-(N-allyloxypropionimidoyl)-3-benzoyloxy-5,5-dimethyl-6-ethoxycarbonyl-2-cyclohexene-1-one | $n_D^{22}1.5282$ |
| 84 | 2-(N-allyloxypropionimidoyl)-3-(4-chlorobenzoyloxy)-5,5-dimethyl-6-ethoxycarbonyl-2-cyclohexene-1-one | $n_D^{22}1.5348$ |
| 85 | 2-(N-allyloxybutyrimidoyl)-3-benzoyloxy-5,5-dimethyl-6-ethoxycarbonyl-2-cyclohexene-1-one | $n_D^{21}1.5252$ |
| 86 | 2-(N-allyloxybutyrimidoyl)-3-(4-chlorobenzoyloxy)-5,5-dimethyl-6-ethoxycarbonyl-2-cyclohexene-1-one | $n_D^{21}1.5302$ |
| 87 | 2-(N-allyloxyacetimidoyl)-3-benzoyloxy-5,5-dimethyl-6-ethoxycarbonyl-2-cyclohexene-1-one | $n_D^{21.5}1.5237$ |
| 88 | 2-(N-allyloxyacetimidoyl)-3-(4-chlorobenzoyloxy)-5,5- | $n_D^{21.5}1.5309$ |

Table 1-continued

| Compound No. | Chemical Name | Physical constant |
|---|---|---|
| 89 | 2-(N-ethoxyacetimidoyl)-3-benzoyloxy-5,5-dimethyl-6-ethoxycarbonyl-2-cyclohexene-1-one | $n_D^{22.5}1.5238$ |
| 90 | 2-(N-ethoxyacetimidoyl)-3-(4-chlorobenzoyloxy)-5,5-dimethyl-6-ethoxycarbonyl-2-cyclohexene-1-one | $n_D^{22}1.5290$ |
| 91 | 2-(N-ethoxybutyrimidoyl)-3-benzoyloxy-5,5-dimethyl-6-ethoxycarbonyl-2-cyclohexene-1-one | $n_D^{23.5}1.5742$ |
| 92 | 2-(N-ethoxybutyrimidoyl)-3-(4-chlorobenzoyloxy)-5,5-dimethyl-6-ethoxycarbonyl-2-cyclohexene-1-one | $n_D^{23.5}1.5265$ |
| 93 | 2-(N-ethoxypropionimidoyl)-3-benzoyloxy-5,5-dimethyl-6-methoxycarbonyl-2-cyclohexene-1-one | $n_D^{24}1.5273$ |
| 94 | 2-(N-ethoxypropionimidoyl)-3-(4-chlorobenzoyloxy)-5,5-dimethyl-6-methoxycarbonyl-2-cyclohexene-1-one | $n_D^{23.5}1.5383$ |
| 95 | 2-(N-allyloxybutyrimidoyl)-3-benzoyloxy-5,5-dimethyl-6-methoxycarbonyl-2-cyclohexene-1-one | $n_D^{24.5}1.5195$ |
| 96 | 2-(N-allyloxybutyrimidoyl)-3-(4-chlorobenzoyloxy)-5,5-dimethyl-6-methoxycarbonyl-2-cyclohexene-1-one | $n_D^{24.5}1.5303$ |
| 97 | 2-(N-ethoxybutyrimidoyl)-3-benozyloxy-5,5-dimethyl-6-methoxycarbonyl-2-cyclohexene-1-one | $n_D^{24.5}1.5165$ |
| 98 | 2-(N-ethoxybutyrimidoyl)-3-(4-chlorobenzoyloxy)-5,5-dimethyl-6-methoxycarbonyl-2-cyclohexene-1-one | $n_D^{24.5}1.5225$ |
| 99 | 2-(N-allyloxypropionimidoyl)-3-benzoyloxy-5,5-dimethyl-6-methoxycarbonyl-2-cyclohexene-1-one | $n_D^{25}1.5205$ |
| 100 | 2-(N-allyloxypropionimidoyl)-3-(4-chlorobenzoyloxy)-5,5-dimethyl-6-methoxycarbonyl-2-cyclohexene-1-one | $n_D^{26}1.5248$ |
| 101 | 2-(N-ethoxyacetimidoyl)-3-benzoyloxy-5,5-dimethyl-6-methoxycarbonyl-2-cyclohexene-1-one | $n_D^{28}1.5211$ |
| 102 | 2-(N-ethoxyacetimidoyl)-3-(4-chlorobenzoyloxy)-5,5-dimethyl-6-methoxycarbonyl-2-cyclohexene-1-one | $n_D^{25.5}1.5325$ |
| 103 | 2-(N-allyloxyacetimidoyl)-3-benzoyloxy-5,5-dimethyl-6-methoxycarbonyl-2-cyclohexene-1-one | $n_D^{25}1.5289$ |
| 104 | 2-(N-allyloxyacetimidoyl)-3-(4-chlorobenzoyloxy)-5,5-dimethyl-6-methoxycarbonyl-2-cyclohexene-1-one | $n_D^{26}1.5298$ |
| 105 | 2-(N-allyloxypropionimidoyl)-3-benzoyloxy-6-ethoxycarbonyl-6-ethyl-2-cyclohexene-1-one | $n_D^{24}1.5225$ |
| 106 | 2-(N-ethoxyacetoimidoyl)-3-benzoyloxy-6-ethoxycarbonyl-6-ethyl-2-cyclohexene-1-one | $n_D^{22}1.5108$ |
| 107 | 2-(N-ethoxypropionimidoyl)-3-benozyloxy-5-(4-chlorophenyl)-2-cyclohexene-1-one | $n_D^{24.5}1.5720$ |
| 108 | 2-(N-ethoxypropionimidoyl)-3-methylsulfonyloxy-5-(4-chlorophenyl)-2-cyclohexene-1-one | m.p. 106–107° C |
| 109 | 2-(N-ethoxypropionimidoyl)-3-benzoyloxy-5-(4-methoxyphenyl)-2-cyclohexene-1-one | $n_D^{24.5}1.5633$ |
| 110 | 2-(N-ethoxypropionimidoyl)-3-methylsulfonyloxy-5-(4-methoxyphenyl)-2-cyclohexene-1-one | m.p. 91–92° C |
| 111 | 2-(N-ethoxypropionimidoyl)-3-benzoyloxy-5-(4-tolyl)-2-cyclohexene-1-one | $n_D^{25.5}1.5632$ |
| 112 | 2-(N-ethoxypropionimidoyl)-3-methylsulfonyl-5-(4-tolyl)-2-cyclohexene-1-one | m.p. 114–115° C |
| 113 | 2-(N-ethoxypropionimidoyl)-3-benzoyloxy-5-(3-chlorophenyl)-2-cyclohexene-1-one | $n_D^{25.5}1.5714$ |
| 114 | 2-(N-ethoxypropionimidoyl)-3-methylsulfonyl-5-(3-chlorophenyl)-2-cyclohexene-1-one | m.p. 88–89° C |
| 115 | 2-(N-ethoxypropionimidoyl)-3-methylsulfonyl-5-(2,4-dichlorophenyl)-2-cyclohexene-1-one | m.p. 73–75° C |
| 116 | 2-(N-ethoxypropionimidoyl)-3-benzoyloxy-5-(2,4-dichlorophenyl)-2-cyclohexene-1-one | $n_D^{27.5}1.5693$ |
| 117 | 2-(N-allyloxypropionimidoyl)-3-benzoyloxy-5-styryl-2-cyclohexene-1-one | $n_D^{25}1.5857$ |
| 118 | 2-(N-ethoxypropionimidoyl)-3-benzoyloxy-5-(2-furyl)-2-cyclohexene-1-one | $n_D^{19}1.5546$ |
| 119 | 2-(N-ethoxypropionimidoyl)-3-benzoyloxy-5-(2-thienyl)-2-cyclohexene-1-one | $n_D^{23.5}1.5729$ |
| 120 | 2-(N-allyloxypropionimidoyl)-3-phenylacetoxy-5,5-dimethyl-2-cyclohexene-1-one | $n_D^{22}1.5249$ |
| 121 | 2-(N-allyloxypropionimidoyl)-3-phenoxyacetoxy-5,5-dimethyl-2-cyclohexene-1-one | $n_D^{22}1.5369$ |
| 122 | 2-(N-ethoxypropionimidoyl)-3-phenylacetoxy-6-isobutyl-2-cyclohexene-1-one | $n_D^{24}1.5172$ |
| 123 | 2-(N-allyloxypropionimidoyl)-3-(2,4-dichlorophenoxyacetoxy)-5,5-dimethyl-2-cyclohexene-1-one | $n_D^{25}1.4082$ |
| 124 | 2-(N-allyloxybutyrimidoyl)-3-(2,4-dichlorophenoxyacetoxy)-5,5-dimethyl-2-cyclohexene-1-one | $n_D^{25}1.5435$ |
| 125 | 2-(N-methylthiomethoxypropionimidoyl)-3-benzoyloxy-5,5-dimethyl-2-cyclohexene-1-one | $n_D^{25}1.5415$ |
| 126 | 2-(N-methoxymethoxypropionimidoyl)-3-benzoyloxy-5,5-dimethyl-2-cyclohexene-1-one | m.p. 84–86° C |
| 127 | 2-(N-methylthiomethoxypropionimidoyl)-3-benzoyloxy-5,5-dimethyl-2-cyclohexene-1-one | $n_D^{23}1.5495$ |
| 128 | 2-(N-methoxymethoxypropionimidoyl)-3-methylsulfonyloxy-5,5-dimethyl-2-cyclohexene-1-one | $n_D^{27}1.4886$ |
| 129 | 2-(N-butoxymethoxypropionimidoyl)-3-benzoyloxy-5,5-dimethyl-2-cyclohexene-1-one | $n_D^{23}1.5138$ |
| 130 | 2-(N-butoxymethoxypropionimidoyl)-3-methylsulfonyloxy-5,5-dimethyl-2-cyclohexene-1-one | $n_D^{23}1.4885$ |
| 131 | 2-(N-allyloxypropionimidoyl)-3-benzoyloxy-5,5-dimethyl-2-cyclohexene-1-one | m.p. 60.5–61.5° C |
| 132 | 2-(N-allyloxybutyrimidoyl)-3-methoxy-5,5-dimethyl-2-cyclohexene-1-one | $n_D^{26}1.3532$ |
| 133 | 2-(N-allyloxypropionimidoyl)-3-benzoyloxy-5,6-tetramethylene-2-cyclohexene-1-one | $n_D^{20.5}1.5499$ |
| 134 | 2-(N-allyloxypropionimidoyl)-3-benzoyloxy-5,5-pentamethylene-2-cyclohexene-1-one | $n_D^{23}1.5475$ |
| 135 | 2-(N-allyloxypropionimidoyl)-3-(2,4-dichlorobenzoyloxy)-5,5-dimethyl-2-cyclohexene-1-one | m.p. 74–75° C |
| 136 | 2-(N-propargyloxybutyrimidoyl)-3-(3,6-dichloro-2-methoxybenzoyloxy)-5,5-dimethyl-2-cyclohexene-1-one | m.p. 87–88° C |
| 137 | 2-(N-allyloxypropionimidoyl)-3-(2,4-dichlorobenzoyloxy)-6,6- | $n_D^{19}1.5490$ |

Table 1-continued

| Compound No. | Chemical Name | Physical constant |
|---|---|---|
| | dimethyl-2-cyclohexene-1-one | |

* m.p.: melting point (° C)
d.p.: decomposition point (° C)
n$_D$: refractive index Hereinafter, the compounds of this invention are represented by Compound No. in Table 1.

As mentioned previously, it has been found that the compounds of the invention possess superior herbicidal activity. The paragraphs which follow described in more detail the utility of this invention.

The compounds of the invention are particularly effective in the control of grass weeds such as annual bluegrass (*Poa annua* L.), water foxtail (*Alopecurus aequalis* Sobol), large crabgrass (*Digitaria adscendens* Henr.), green foxtail (*Seturia viridis* Beauv), wild oat (*Avena fatua* L) etc. and they hardly injure broad leaf crops such as adzuki beam (*Phaseolus angularis* W. F. Wright) and soy bean (*Glycine max* Merrill) and sugar beets (*Beta vulgaris* L.) which easily suffer phyto-toxicity. Namely, the compound of the invention are the selective herbicide.

It is already known that 4-hydroxy-6-methyl-α-pyrone derivatives has herbicidal properties as shown in Japanese Pat. Publication No. 16916/1971.

But in order to destroy completely the said grass weeds, a large amount of the above herbicidal chemical is required and this is one drawback for above mentioned herbicidal compound.

In the other words, according to the descriptions of above mentioned prior art and the results of the later additional experiments by the inventors, a chemical amount containing 500 g of effective ingredient, in proportion to 10 are ("are" is 100 square meters) of area is able to give an expected effect in the case of employing it practically, but another chemical amount containing 250 g of effective ingredient, in proportion to 10 are of area is not able to wither grass weeds to death, in the other weeds, it cannot give a perfect herbicidal effect.

But, in the event of employing the compound of the present invention as a herbicide, a chemical amount containing 250 g of effective component, as a matter of course, further a chemical amount containing 125 g or less of effective ingredient, in proportion to 10 are of area, in compliance with the same treating method of conventional herbicide exhibits a strong herbicidal effect and thereby a perfect prevention and extermination of weeds can be expected.

In case of foliar treatment using the compounds of the present invention, even the same amount of chemical which kills completely barnyard grass of grass weeds gives no damages to broadleaf plants such as radish (*Raphanus sativus* L.), soy bean, garden pea (*Pisum sativum* L.), spinach (*Spinacia oleracea* L.) sugar beets and carrot (*Daucus carota* L.) at all, and in case of soil treatment before germination, even the same amount of chemicals which prevents large crabgrass germinating gives no damages to seeds of broad leaf plants at all.

As mentioned above, a security to the broadleaf crop against phytotoxicity of the herbicide is extremely high and as to its application, in the other words, its applicable time, its applying location and its applying concentration, it has a very broad extent and it can be used in the wider extent.

It is another advantage of the present invention that a residual toxicity in the soil or the plant and an acute toxicity for worm blooded animals and fish are not feared because the said compounds can be used with a low chemical concentration.

The compounds of this invention can be applied directly to the soil as pre-emergence treatment or to plant foliage, as post-emergence treatment, or they can be mixed intimately with the soil, preferably post-emergence treatment to plant foliage, and may be applied to soil or plant foliar at rates of 50–1000 g per 10 are, preferably 50–200 g per 10 are, more preferably about 100 g per 10 are.

The method of the present invention comprehends the employment of a liquid or solid composition containing one or more of the present compounds as an active ingredient.

The active ingredient of this invention may be formulated by mixing with suitable carriers in a form generally used in agricultural chemicals such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, benzene, xylene, cyclohexane, cyclohexanone, dimethylformamide, alcohol, acetone, and others are used. Sometimes surface active agent is added in order to give a homogeneous and stable formulation.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides, acaricides, fungicides, herbicides and nematocides.

As for known herbicides it is recommended that the compound of the present invention is applied admixed with urea derivatives such as 3-(3,4-dichlorophenyl)-1-methoxy-1-nmethylurea, or N-(3,4-dichlorophenyl)N', N'-dimethylurea, triazine derivatives such as 2-chloro-4-ethylamino-6-isopropylamino-s-triazine, or 2-chloro-4,6-bis(ethylamino)-s-triazine and amide derivatives such as N-1-naphthyl-phthalamic acid.

The concentrations of the active ingredients in the herbicidal composition of this invention vary according to type of formulation, and they are, for example, used in a range of 5 – 80 weight percent, preferably 10 – 60 weight percent, in wettable powder, 5 – 70 weight percent, preferably 20 – 60 weight percent, in emulsifiable concentrates, and 0.5 – 30 weight percent, preferably 1 – 10 weight percent in dust formulation.

Thus, a wettable powder or an emulsifiable concentrate produced thereto is diluted with water to a specified concentration and thereby, it is used as a liquid suspension or a liquid emulsion for treating soils or plant foliars. Further, a dust formulation is directly used for the soil treatment or the foliar treatment.

The non-limiting examples for the herbicidal composition are illustrated as follows:

EXAMPLE 15

Wettable Powder

| | Parts by weight |
|---|---|
| Compound 8 | 20 |
| Diatomaceous earth | 35 |
| Sodium alkylsulfate | 6 |
| Talc | 35 |
| White carbon | 4 |

These are mixed homogeneously and reduced to fine particles. Consequently, wettable powder containing 20% of active ingredient is obtained. In practical use, it is diluted to a certain concentration with water and is sprayed as a suspension.

EXAMPLE 16

Emulsifiable Concentrate

| | Parts by weight |
|---|---|
| Compound 1 | 40 |
| Xylene | 33 |
| Dimethylformamide | 15 |
| Polyoxyethylene phenylether | 12 |

These are mixed and dissolved.

Consequently, emulsifiable concentrate containing 40% of the active ingredient is obtained. In practical use, it is diluted to certain concentration with water and then is sprayed an emulsion.

EXAMPLE 17

Dust Formulation

| | Parts by weight |
|---|---|
| Compound 14 | 5 |
| Talc | 38.5 |
| Bentonite | 10 |
| Clay | 38.5 |
| Sodium alkylsulfate | 8 |

These are mixed homogeneously and reduced to fine particles. Fine particles are made into granules having the diameter in the range of 0.5 – 1.0 mm by granulator.

Consequently, dust formulation containing 50% of the active ingredient is obtained. In practical use it is directly applied.

The superior herbicidal effect of the novel compounds of this invention is clearly illustrated by the following test.

Test 1. Pre-emergence treatment (soil treatment in paddy condition)

About 60 seeds of barnyard grass were planted in a pot having 60 square centimeters and covered slightly with soil. Water was poured into the pot until the surface of soil became wet.

10 ml of an aqueous emulsion prepared by diluting an emulsifiable concentrate with water to a specified concentration was sprayed on the pot. The pots were kept in a green house and water was added to the pots daily in order to keep the water level. Two weeks after spraying, the degrees of damage to the plant were observed and estimated by the values of 0 – 5 which have the following meanings:

0: no effect
1: partial plant slightly injured
2: plant slightly injured
3: plant moderately injured.
4: plant severely injured
5: plant completely killed or no germination The results were shown in Table 2.

Table 2

| Test Compound No. | Application rate (g/10 ares) | | |
|---|---|---|---|
| | 30 | 15 | 7.5 |
| 1 | 5 | 3 | 1 |
| 2 | 5 | 4 | 3 |
| 3 | 5 | 4 | 3 |
| 4 | 4 | 3 | 1 |
| 5 | 5 | 4 | 3 |
| 6 | 5 | 3 | 2 |
| 7 | 4 | 4 | 3 |
| 8 | 5 | 4 | 3 |
| 11 | 5 | 4 | 3 |
| 12 | 4 | 3 | 1 |
| 13 | 5 | 4 | 3 |
| 14 | 5 | 4 | 3 |
| 15 | 5 | 5 | 4 |
| 16 | 5 | 4 | 4 |
| 18 | 4 | 3 | 1 |
| 19 | 5 | 4 | 2 |
| 20 | 5 | 4 | 3 |
| 21 | 4 | 3 | 2 |
| 22 | 4 | 3 | 2 |
| 23 | 5 | 4 | 3 |
| 24 | 4 | 4 | 3 |
| 25 | 4 | 3 | 1 |
| 26 | 5 | 4 | 3 |
| 27 | 5 | 4 | 2 |
| 28 | 4 | 3 | 1 |
| 29 | 4 | 3 | 2 |
| 30 | 5 | 4 | 3 |
| 31 | 4 | 4 | 3 |
| 32 | 5 | 4 | 3 |
| 33 | 5 | 4 | 3 |
| 34 | 4 | 2 | 1 |
| 35 | 5 | 4 | 3 |

Table 2-continued

| Test Compound No. | Application rate (g/10 ares) | | |
|---|---|---|---|
| | 30 | 15 | 7.5 |
| 36 | 5 | 4 | 3 |
| 37 | 4 | 3 | 1 |
| 39 | 4 | 3 | 2 |
| 44 | 5 | 4 | 3 |
| Comparative compound | | | |

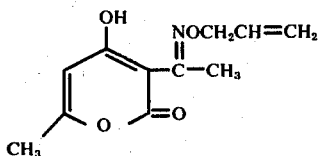

| | 1 | 0 | 0 |
|---|---|---|---|
| Untreated | | 0 | |

Test 2. Post-emergence treatment
(foliar treatment in paddy condition)

About 50 seeds of barnyard grass were planted in a pot having 60 square centimeters and covered slightly with soil. Said pot was filled with water to about 3 cm above the surface of the soil when the plant was grown to first leaf-stage.

An aqueous emulsion prepared by diluting an emulsifiable concentrate with water to a specified concentration was sprayed on the pot. The pots were kept in a green house and water was added to the pot daily in order to keep the water level. Two weeks after spraying, the degrees of damage to the test plant was observed and estimted by the values of 0 - 5 which have the same meanings as those of Test 1.

The results were shown in Table 3.

Table 3

| Test Compound No. | Application rate (g/10 ares) | | |
|---|---|---|---|
| | 125 | 62.5 | 31.5 |
| 1 | 5 | 4 | 3 |
| 2 | 5 | 4 | 2 |
| 3 | 5 | 5 | 3 |
| 4 | 5 | 4 | 3 |
| 5 | 5 | 5 | 3 |
| 6 | 5 | 5 | 2 |
| 7 | 5 | 5 | 4 |
| 8 | 5 | 5 | 5 |
| 11 | 5 | 4 | 3 |
| 12 | 5 | 4 | 2 |
| 13 | 5 | 5 | 2 |
| 14 | 5 | 5 | 4 |
| 15 | 5 | 5 | 5 |
| 16 | 5 | 5 | 5 |
| 18 | 5 | 4 | 2 |
| 19 | 5 | 5 | 3 |
| 20 | 5 | 5 | 4 |
| 21 | 5 | 5 | 2 |
| 22 | 5 | 5 | 3 |
| 23 | 5 | 5 | 5 |
| 24 | 5 | 4 | 2 |
| 25 | 5 | 4 | 2 |
| 26 | 5 | 5 | 3 |
| 27 | 5 | 4 | 3 |
| 28 | 5 | 4 | 2 |
| 29 | 5 | 5 | 4 |
| 30 | 5 | 5 | 4 |
| 31 | 5 | 4 | 2 |
| 32 | 5 | 4 | 3 |
| 33 | 5 | 5 | 3 |
| 34 | 5 | 4 | 4 |
| 35 | 5 | 4 | 2 |
| 36 | 5 | 5 | 2 |
| 37 | 5 | 4 | 2 |
| 38 | 5 | | |
| 39 | 5 | 4 | 2 |
| 40 | 5 | | |
| 41 | 5 | | |
| 42 | 5 | | |
| 43 | 5 | | |
| 44 | 5 | 5 | 2 |
| Comparative compound | | | |

Table 3-continued

| Test Compound No. | Application rate (g/10 ares) | | |
|---|---|---|---|
| | 125 | 62.5 | 31.5 |
| 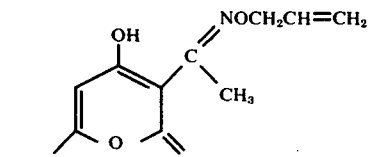 | 3 | 1 | 0 |
| 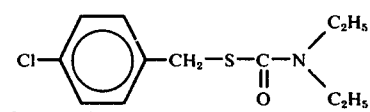 | 3 | 1 | 0 |
| Untreated | | 0 | |

Test 3. Pre-emergence treatment

Seeds of large crab-grass were planted in a pot having 100 square centimeters. An aqueous emulsion prepared by diluting an emulsifiable concentrate with water to a specified concentration was sprayed on the surface of the soil before emergence. The pots were kept in a green house. 21 days after spraying, the degrees of damage to the test plants were observed and estimated by the value of 0 – 5 which have the same meanings as those of Test 1.

The results were shown in Table 4.

Table 4

| Test Compound No. | Application rate (g/10 ares) | | | |
|---|---|---|---|---|
| | 250 | 125 | 60 | 30 |
| 1 | | 5 | 4 | 3 |
| 2 | | 5 | 4 | 2 |
| 3 | | 5 | 5 | 3 |
| 4 | | 5 | 4 | 3 |
| 5 | | 5 | 5 | 3 |
| 6 | | 5 | 5 | 3 |
| 7 | | 5 | 4 | 3 |
| 8 | | 5 | 5 | 3 |
| 11 | | 5 | 4 | 3 |
| 12 | | 4 | 3 | 2 |
| 13 | | 5 | 5 | 3 |
| 14 | | 5 | 4 | 3 |
| 15 | | 5 | 5 | 3 |
| 16 | | 5 | 5 | 3 |
| 18 | | 4 | 4 | 2 |
| 19 | | 5 | 4 | 3 |
| 20 | | 5 | 4 | 3 |
| 21 | | 5 | 4 | 2 |
| 22 | | 5 | 5 | 3 |
| 23 | | 5 | 4 | 3 |
| 24 | | 5 | 4 | 2 |
| 25 | | 5 | 4 | 2 |
| 26 | | 5 | 5 | 3 |
| 27 | | 5 | 4 | 3 |
| 28 | | 4 | 4 | 2 |
| 29 | | 5 | 4 | 2 |
| 30 | | 5 | 5 | 3 |
| 31 | | 4 | 4 | 2 |
| 32 | | 5 | 4 | 2 |
| 33 | | 5 | 4 | 3 |
| 34 | | 5 | 4 | 2 |
| 35 | | 5 | 4 | 3 |
| 36 | | 5 | 4 | 3 |
| 37 | | 5 | 4 | 3 |
| 39 | | 5 | 4 | 2 |
| 44 | | 5 | 4 | 3 |
| Comparative compound 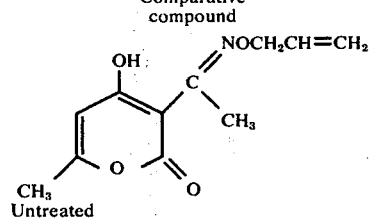 | 4 | 2 | 0 | 0 |
| Untreated | | | 0 | |

Test 4. Post-emergence treatment (foliar treatment)

Seeds of large crab-grass was planted in a pot having 100 square centimeters. When plants became 2 – 4 leaves stage, an aqueous emulsion prepared by diluting an emulsifiable concentrate with water to a specified concentration was sprayed on the foliar of the test plant at a rate of 100 liters per 10 are. The plants were kept in a green house.

21 days after spraying, the degrees of damage to the test plant were observed and estimated by the value of 0 – 5 which have the same meanings as those of Test 1. The results were shown in Table 4.

Table 5

| Test Compound No. | Application rate (g/10 ares) | | |
|---|---|---|---|
| | 100 | 50 | 25 |
| 1 | 5 | 5 | 4 |
| 2 | 5 | 4 | 3 |
| 3 | 5 | 5 | 5 |
| 4 | 5 | 3 | 3 |
| 5 | 5 | 5 | 5 |
| 6 | 5 | 5 | 4 |
| 7 | 5 | 5 | 4 |
| 8 | 5 | 5 | 5 |
| 11 | 5 | 5 | 4 |
| 12 | 5 | 5 | 3 |
| 13 | 5 | 5 | 5 |
| 14 | 5 | 5 | 4 |
| 15 | 5 | 5 | 5 |
| 16 | 5 | 5 | 5 |
| 18 | 5 | 4 | 3 |
| 19 | 5 | 5 | 4 |
| 20 | 5 | 5 | 4 |
| 21 | 5 | 5 | 4 |
| 22 | 5 | 5 | 5 |
| 23 | 5 | 5 | 5 |
| 24 | 5 | 4 | 4 |
| 25 | 5 | 3 | 3 |
| 26 | 5 | 5 | 5 |
| 27 | 5 | 5 | 4 |
| 28 | 5 | 3 | 3 |
| 29 | 5 | 5 | 5 |
| 30 | 5 | 5 | 4 |
| 31 | 5 | 3 | 3 |
| 32 | 5 | 4 | 3 |
| 33 | 5 | 5 | 5 |
| 34 | 5 | 3 | 3 |
| 35 | 5 | 5 | 4 |
| 36 | 5 | 5 | 5 |
| 37 | 5 | 4 | 4 |
| 39 | 5 | 5 | 4 |
| 44 | 5 | 5 | 4 |
| Comparative compound | | | |
| 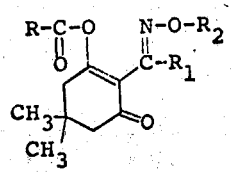 | 3 | 2 | 0 |
| 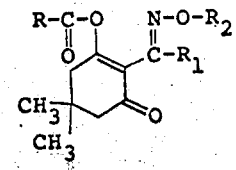 | 3 | 1 | 0 |
| Untreated | | 0 | |

What is claimed is:

1. A compound of the formula

R-C-O    N-O-R₂
 ‖        ‖
 O        C-R₁
    CH₃
    CH₃ wherein
- $R_1$ is selected from the group consisting of phenyl and straight or branched chain alkyl;
- $R_2$ is selected from the group consisting of straight or branched chain lower alkyl, straight or branched chain lower alkenyl, lower alkynyl, lower alkoxymethyl, lower alkylthiomethyl and benzyl;
- R is selected from the group consisting of phenyl and phenyl substituted with halogen, nitro, methyl or methoxy.

2. A compound of the formula

R-C-O    N-O-R₂
 ‖        ‖
 O        C-R₁
    CH₃
    CH₃ wherein

R₁ is selected from the group consisting of ethyl and propyl;

R₂ is selected from the group consisting of ethyl, propyl, allyl and propargyl;

R is selected from the group consisting of phenyl and substituted phenyl having at least one substituent selected the group consisting of chlorine, methyl, methoxy and nitro.

3. 2-(N-allyloxypropionimidoyl)-3-(4-chlorobenzoyloxy)-5,5-dimethyl-2-cyclohexene-1-one.

4. 2-(N-allyloxybutyrimidoyl)-3-benzoyloxy-5,5-dimethyl-2-cyclohexene-1-one.

5. 2-(N-allyloxypropionimidoyl)-3-(4-nitrobenzoyloxy)-5,5-dimethyl-2-cyclohexene-1-one.

6. 2-(N-allyloxypropionimidoyl)-3-benzoyloxy-5,5-dimethyl-2-cyclohexene-1-one.

7. 3-benzoyloxy-5,5-dimethyl-2-N-propargyloxybutyrimidoyl-2-cyclohexene-1-one.

8. 2-(N-allyloxypropionimidoyl)-3-(3-methoxybenzoyloxy)-5,5-dimethyl-2-cyclohexene-1-one.

9. 2-(N-allyloxypropionimidoyl)-3-(3-chlorobenzyloxy)-5,5-dimethyl-2-cyclohexene-1-one.

10. 3-(4-methylbenzoyloxy)-5,5-dimethyl-2-(N-propargyloxybutyrimidoyl)-2-cyclohexene-1-one.

11. A method for the control of weeds comprising applying a composition containing a compound of claim 1 in an amount sufficient to exert herbicidal action to a locus to be protected.

12. A method for the control of weeds comprising applying a composition containing a compound of claim 2 in an amount sufficient to exert herbicidal action to a locus to be protected.

13. A method for the control of weeds comprising applying a composition containing a compound of claim 3 in an amount sufficient to exert herbicidal action to a locus to be protected.

14. A method for the control of weeds comprising applying a composition containing a compound of claim 4 in an amount sufficient to exert herbicidal action to a locus to be protected.

15. A method for the control of weeds comprising applying a composition containing a compound of claim 5 in an amount sufficient to exert herbicidal action to a locus to be protected.

16. A method for the control of weeds comprising applying a composition containing a compound of claim 6 in an amount sufficient to exert herbicidal action to a locus to be protected.

17. A method for the control of weeds comprising applying a composition containing a compound of claim 7 in an amount sufficient to exert herbicidal action to a locus to be protected.

18. A method for the control of weeds comprising applying a composition containing a compound of claim 8 in an amount sufficient to exert herbicidal action to a locus to be protected.

19. A method for the control of weeds comprising applying a composition containing a compound of claim 9 in an amount sufficient to exert herbicidal action to a locus to be protected.

20. A method for the control of weeds comprising applying a composition containing a compound of claim 10 in an amount sufficient to exert herbicidal action to a locus to be protected.

* * * * *